(12) United States Patent
Hsu et al.

(10) Patent No.: US 8,801,614 B2
(45) Date of Patent: Aug. 12, 2014

(54) ON-AXIS SHEAR WAVE CHARACTERIZATION WITH ULTRASOUND

(75) Inventors: Stephen J. Hsu, Issaquah, WA (US); Manoj G. Menon, Sammamish, WA (US); David P. Duncan, Renton, WA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 23 days.

(21) Appl. No.: 13/371,287

(22) Filed: Feb. 10, 2012

(65) Prior Publication Data

US 2013/0211253 A1  Aug. 15, 2013

(51) Int. Cl.
*A61B 8/00* (2006.01)
(52) U.S. Cl.
USPC .......................................................... 600/438
(58) Field of Classification Search
None
See application file for complete search history.

(56) References Cited

U.S. PATENT DOCUMENTS

| | | | |
|---|---|---|---|
| 5,606,971 A | | 3/1997 | Sarvazyan |
| 5,810,731 A * | | 9/1998 | Sarvazyan et al. ............ 600/438 |
| 2006/0052696 A1* | | 3/2006 | Shiina et al. .................. 600/437 |
| 2010/0016718 A1 | | 1/2010 | Fan et al. |
| 2010/0286516 A1* | | 11/2010 | Fan et al. ....................... 600/438 |
| 2012/0136250 A1* | | 5/2012 | Tabaru et al. ................. 600/438 |
| 2012/0253194 A1* | | 10/2012 | Tamura ......................... 600/438 |

\* cited by examiner

*Primary Examiner* — Elmer Chao

(57) ABSTRACT

Shear wave imaging is provided in medical diagnostic ultrasound. The generation of a shear wave with acoustic energy forms a pseudo shear wave (an apparent wave) traveling towards the transducer. Transmission and reception along a single line may be used to detect the pseudo shear wave traveling towards the transducer. The shear velocity or characteristic may be determined without reception along multiple laterally spaced scan lines. One transmission to generate the shear wave may be used. With multi-beam receive or without, calculating shear velocity from along a single line allows rapid determination.

20 Claims, 3 Drawing Sheets

ON-AXIS SHEAR WAVE CHARACTERIZATION WITH ULTRASOUND

BACKGROUND

The present embodiments relate to shear wave velocimetry. Ultrasound may be used to detect a shear wave in tissue. Shear is a viscoelastic property of tissue. The shear wave velocity or shear characteristics derived from the shear velocity may assist in diagnosis, such as indicating the health of tissue.

In shear wave velocimetry, acoustic radiation force is used to excite a region of interest in soft tissue. This excitation produces shear waves that are tracked at laterally offset positions. In an ultrasound system without parallel-receive capabilities, these shear waves are tracked by transmitting multiple excitations for sequentially generating multiple shear waves and superimposing the recorded response at various laterally offset positions.

Shear wave images may be generated. A characteristic of the shear wave in the tissue is determined for different spatial locations. An image of the characteristic as a function of space is generated. A large number of transmissions and receptions are used to estimate shear wave information in a large region, resulting in a slow frame rate. Multiple shear waves may be sequentially generated to determine the shear velocity any one or more locations. The number of transmissions and receptions may be reduced by forming multiple receive beams in response to each transmission. However, expensive or complex hardware capability is needed for forming multiple receive beams in response to a transmission.

BRIEF SUMMARY

By way of introduction, the preferred embodiments described below include methods, instructions, and systems for shear wave imaging in medical diagnostic ultrasound. The generation of a shear wave with acoustic energy forms a pseudo shear wave or apparent wave traveling towards the transducer. Transmission and reception along a single line may be used to detect the pseudo shear wave traveling towards the transducer. The shear velocity or characteristic may be determined from the apparent velocity without reception along multiple laterally spaced scan lines. One transmission to generate the shear wave may be used, but multiple transmissions to generate shear waves may alternatively be used. With multi-beam receive or without, calculating shear velocity from along a scan line allows rapid determination such that the velocity may be determined multiple times in a heart cycle.

In a first aspect, a method is provided for shear wave imaging in medical diagnostic ultrasound. A transducer transmits acoustic energy to a focal region. A shear wave is generated from the transmitting. A pseudo shear wave is detected at a plurality of locations along a line extending from the transducer. The pseudo shear wave is formed with the shear wave. A processor calculates a shear velocity from the detected pseudo shear wave in response to a single event of the transmitting and without repeating the transmitting. An image is displayed as a function of the shear velocity.

In a second aspect, a non-transitory computer readable storage medium has stored therein data representing instructions executable by a programmed processor for shear wave imaging in medical diagnostic ultrasound. The storage medium includes instructions for tracking a wave along a line substantially parallel with a scan line, determining an apparent velocity of the wave along the line, scaling the apparent velocity by a constant and a transmit F number, a result of the scaling comprising a shear velocity, and displaying an image as a function of the shear velocity.

In a third aspect, a method is provided for shear wave imaging in medical diagnostic ultrasound. An apparent wave traveling towards a transducer is located. The apparent wave is responsive to a shear wave traveling laterally relative to the transducer. A processor calculates a shear velocity from the apparent wave. An image as a function of the shear velocity is displayed.

In a fourth aspect, a system is provided for shear wave imaging in medical diagnostic ultrasound. A beamformer is configured to receive along a single scan line in response to a single transmit event. A processor is configured to estimate a shear velocity from data representing response along the scan line. A display device is operable to output an image as a function of the shear velocity.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Shear velocity is estimated. Acquiring shear velocity information rapidly may improve the clinical workflow, allowing analysis of cardiac structures. From a single acoustic radiation force (ARFI) excitation, a wave velocity may be measured. During the transmission of a single ARFI excitation, shear waves are launched in three dimensions. The outward propagation of the shear wave away from the region of excitation constructively produces a pseudo shear wave propagating towards the transducer. This pseudo shear wave is measured at multiple locations along a scan line or other line intersecting the transducer. From these measurements, a shear wave velocity of the material may be determined. Although not a shear wave, in a linear isotropic medium, the shear wave velocity may be calculated from the apparent velocity of the pseudo shear wave by a simple scale factor and normalization by the excitation F/#.

Figure 1:
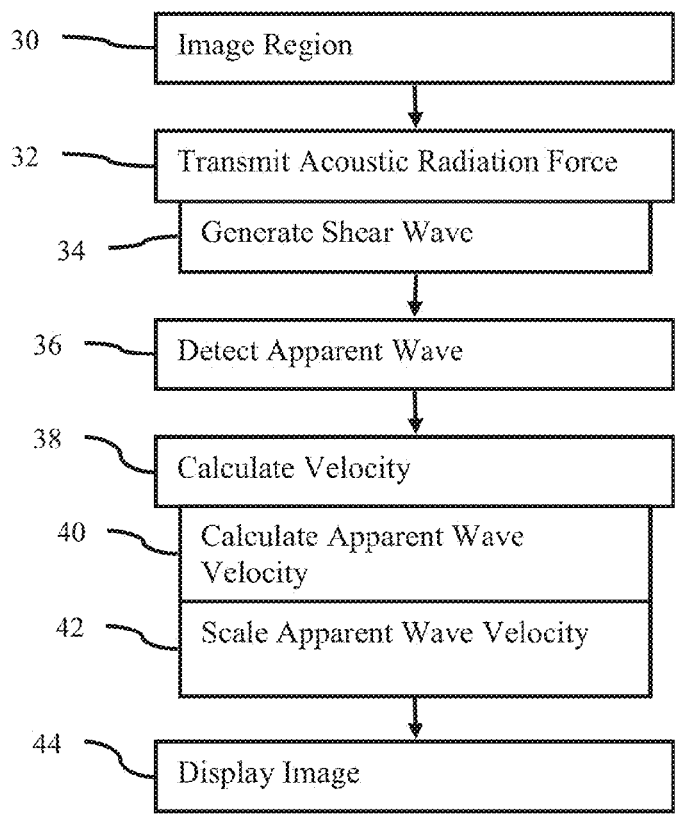
FIG. 1 is a flow chart diagram of one embodiment of a method for shear wave imaging in medical diagnostic ultrasound.

FIG. 1 shows a method for shear wave imaging in medical diagnostic ultrasound. The method is implemented by the system of FIG. 6 or a different system. Additional, different, or fewer acts may be provided. For example, act 30 for imaging, such as to assist in locating a region to estimate shear, is not performed. As another example, data is output for storage or transfer in addition to or as an alternative to displaying an image in act 44. The acts are performed in the order described or shown, but may be performed in other orders.

In act 30, a region is imaged. The region is a two or three-dimensional region of a patient. For imaging a volume, the data is rendered to a planar presentation or three-dimensional representation on a two-dimensional display. Alternatively, a one-dimensional region is imaged.

Any type of imaging may be used. For example, ultrasound imaging is provided. B-mode, color flow (Doppler velocity, energy, and/or variance), elasticity, acoustic force radiation imaging, harmonic imaging, or other now known or later developed imaging mode is used to generate an image or sequence of images. Combination images using multiple modes may be provided, such as B-mode in combination with one of the other modes.

Acoustic force radiation imaging detects displacement of tissue in response to pressure applied to the tissue with acoustic energy. An elasticity image indicates the stiffness of tissue, so may provide an indication of abnormal tissue. B-mode mode images may show a tissue region differently than surrounding tissue, indicating possible abnormal tissue. A color flow image may indicate tissue associated with less movement than expected or other abnormal movement. Other modes of imaging may provide an indication of possible abnormal tissue. A medical professional may have other information indicating a location in the patient associated with a possible abnormality, such as other images (e.g., x-ray, computed tomography, or magnetic resonance images), lab tests, or training.

A location for shear velocity estimation is identified. The location is a point, line, area, or volume. More than one location may be identified. The location is in the two or three-dimensional region that is imaged, such as identifying abnormal tissue in an image. Imaging aids the workflow and assists in limiting the area for which shear velocity or other tissue property is to be measured. The location may be identified independent of the imaging, such as desiring information for a specific part of an organ.

A user identifies the location. The user examines one or more images, such as examining an ongoing sequence of images (e.g., in real-time with scanning). The user may examine one or more previously acquired images, such as from CINE memory or image archive. The user enters the location for further study with a user interface. For example, the user navigates a pointer over the image to the location of a possible abnormality, and then clicks or activates the user input to indicate the location.

Alternatively, a processor automatically identifies the location from the ultrasound imaging. Any image or data processing may be used to identify the location. For example, an image is filtered to isolate a region of interest. As another example, region growing, border detection, or other techniques are used alone or in combination. In one embodiment, an image is segmented. For example, an elasticity image is divided into areas associated with different levels of intensity. A low pass filter may be applied to minimize noise before or after segmentation. A segment is selected as the location. For example, the location corresponding to the brightest, darkest, or mean intensity is selected. For elasticity imaging, the darkest location may indicate the stiffest tissue, so the darkest location is selected. Other segmenting and selecting may be used.

To determine the shear velocity or other shear characteristic, acoustic energy is transmitted in act 32 to or near the selected location. The acoustic energy is transmitted along a scan line and focused at a point or region adjacent to or within the identified location. The location or part of the location may be set as the focal region. A transducer converts relatively delayed waveforms into acoustic waveforms. The relative delays establish the focal region. A shear wave is generated by the focused acoustic energy. The acoustic energy is a single, few (e.g., 2-10) or many (e.g., more than 10) pulses for generating the shear wave in act 34.

In one transmit event of act 32 for generating the shear wave in act 34, only one continuous transmission is used. The waves may have multiple cycles. Some elements of the aperture may transmit at entirely different times than other elements for constructive interference at the focal region. The event may last for a short time or a long time depending on the number of cycles. The event provides for continuous application of acoustic energy at a focal region. Ceasing application and then starting again is another event. Rather than repeat the event, only one transmit event generates a shear wave, allowing detection of the shear velocity. The transmission may be repeated to the same or different location or focal region in other transmit events for generating another shear wave.

The acoustic energy propagates from the transducer to the focal region. The acoustic energy generally propagates along the scan line. The scan line is the center of the transmit beam and extends from an origin on the transducer (e.g., center of the aperture) to the focal region. The scan line for the transmit beam may be positioned to intersect or to pass adjacent to the focal region, such as passing by another point in the abnormal tissue or even passing by the abnormal tissue.

The acoustic energy constructively combines at the focal region to provide a desired amplitude. For example, a transmit pulse or pulses used for acoustic radiation force imaging is transmitted in act 32 to generate the shear wave in act 34. Lower amplitude transmit pulses may be used, such as pulses at an amplitude similar to transmit pulses for B-mode imaging. The duration, which may be on the order of 100 times longer than B-mode pulses, results in the transfer of enough energy to generate the shear wave. The amplitude and duration, given a size of the focal region, generates a shear wave in act 34.

Other sources of stress in the tissue to generate the shear wave may be used. An external source of pressure other than the transducer may be used, such as a thumper causing a shear wave on the imaging axis. Manually or internally generated sources of stress causing a shear wave on the imaging axis may be used. The stress may be added or released. The applied stress may be an impulse, cyclical, repeating, or a non-impulse stress. The applied stress may be represented by an impulse. A substantial single pressure wave is generated. The impulse may be generated by a cyclical pulsed waveform of any number of cycles (e.g., tens or hundreds of cycles). The resulting acoustic radiation force is transmitted as an impulse for applying stress to tissue. The impulse wavefront propagates to the region of interest.

Figure 2:
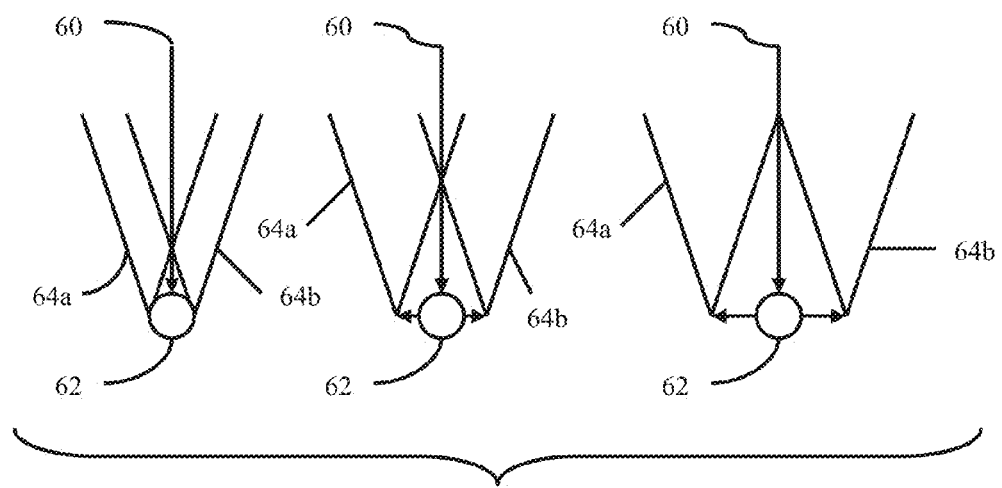
FIG. 2 is an example illustration of a pseudo shear wave associated with a shear wave.

FIG. 2 shows transmission of the acoustic energy along the scan line 60 to the focal region 62. The shear wave is generated at the focal region 62. In general, the shear wave is represented by two "V" shapes 64a and 64b as the wave spreads out from the focal region 62. The acoustic energy, even focused at the focal region 62, generally results in shear being generated in a cone shape.

The shear wave propagates laterally, as represented by the horizontal arrows extending away from the focal region 62. The shear wave propagates in various directions, including a direction perpendicular to the direction of the applied stress as represented by the vertical arrows. Propagation in other directions may occur. With a linear 1-D array, one cross section of the propagating wave is measured. Additionally, for a linear 1-D array, the elevational width of the excitation pulse is much smaller than the lateral dimension, therefore, the F/# is very big, and the psuedo shearwave propagating in that dimension is very fast and thus those displacements propagate out of our field of view very quickly.

The lateral propagation results in the cone or V shapes 64a, 64b spreading apart over time, where the "V represents the shear wave fronts. Along the scan line 60, the laterally progressing shear waves of the cone (i.e., "V" in two dimensions) start at one location and appear to move towards the transducer over time. FIG. 2 shows three different times with the V shapes 64a, 64b intersecting the scan line 60 at different depths. The depth of the peak of the apparent wave becomes shallower over time.

The shear wave propagates through tissue more slowly than the longitudinal wave along the acoustic wave emission direction. The pseudo shear wave appearing to be traveling along the scan line 60 propagates faster than the shear wave, but has a velocity related to the shear velocity. The apparent velocity scales with 1/F#, so if the F#>1, then the apparent wave propagate fasters. If the F#<1, then the apparent wave is slower.

This pseudo shear wave is detected in act 36. The pseudo shear wave is detected at one or more locations substantially along the scan line 60. "Substantially" accounts for aberrations or other inaccuracies in ultrasound scanning. The line used for detection may be other than the scan line 60. For example, the line used for detecting is substantially parallel but spaced from or is intersecting but at a non-zero angle to the scan line 60 along which the acoustic energy is transmitted in act 32. The line used for detection intersects the transducer, but may be at an angle not intersecting the transducer.

The pseudo shear wave is tracked by detection at one or more locations. In one embodiment, the pseudo shear wave is detected at multiple locations along the line, such as at three locations. More or fewer locations may be used. The locations are at different depths than the focal region, such as being spaced between the focal region and the transducer while being within the abnormal tissue or region of interest. The use of multiple locations allows determination of a distance as a function of time between two locations. Any number of depths may be used, such as about 200 for 5 mm or 400 for 10 mm. Additional locations may provide redundancy. In another embodiment, the apparent velocity is determined from the focal region to just one location.

The pseudo shear wave appears to travel towards the transducer or along the line. The monitoring uses transmissions and receptions multiple times along the line to track the pseudo shear wave. The transmissions are for monitoring and do not generate a shear wave or are not used to generate a shear wave that is tracked.

To detect, ultrasound data is obtained. At least some of the ultrasound data is responsive to the pseudo shear wave. B-mode data along the line is obtained at different times. Doppler, color flow, or other ultrasound mode may be used instead to monitor. The monitoring is performed for just the one line, but may be performed along additional lines for redundancy or averaging of the results. For example, four receive beams are formed in response to each monitoring transmission. After transmitting the acoustic force to generate the shear wave, B-mode transmissions along a single scan line and receptions along four adjacent scan lines are performed repetitively. Any number of repetitions may be used, such as about 120 times. Some of the ultrasound data, such as at the beginning or end of the repetitions, may not be responsive to the pseudo shear wave. For systems without multi-beam capability or even for systems with multi-beam capability, only a single receive scan line may be used for monitoring.

As the pseudo shear wave propagates along the line, the B-mode intensity may vary. The variation in intensity may be used to detect the pseudo shear wave. The variation may be due to displacement of tissue caused by the pseudo shear wave.

Figure 3:
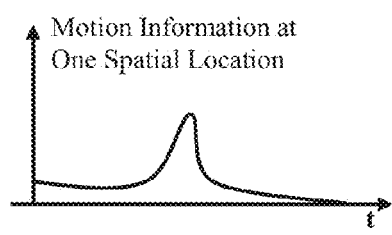
FIG. 3 is an example graphical representation of a time profile of tissue motion information, such as displacements, as a function of time at a location responsive to an pseudo shear wave.

The displacement may be more directly detected. In one embodiment, the detection uses a temporal profile of displacement at the location. A sequence of data is provided representing a time profile of tissue motion resulting from the shear wave. For example, data from a plurality of spatial locations (e.g., along the scan line) is correlated as a function of time. The displacement may be measured from tissue data, such as B-mode ultrasound data. Correlation, cross-correlation, minimum sum of absolute differences or other similarity measure is used to determine the displacement between scans. The displacements are determined along one, two, or three dimensions. For each depth or spatial location, a correlation over a plurality of depths or spatial locations (e.g., kernel of 64 depths with the center depth being the point for which the profile is calculated) is performed. The spatial offset with the highest or sufficient correlation at a given time indicates the amount of displacement. The displacement is determined at different times for each of the depths. For each location, the displacement as a function of time is determined. FIG. 3 shows an example plot of displacement over time for a location. By monitoring the displacement over time, the time at which the apparent wave arrives, peaks, or leaves from the location may be determined.

Since the monitoring is along a scan line or line intersecting with the transducer, the same data representing the line over time may be used to monitor the different depths. To monitor a larger region or more lines, additional receive beams are formed in response to the monitoring transmit beam. Alternatively, another shear wave is generated and the transmit beams and receive beams are provided at a different distance from the shear wave generation point. For each receive beam or scan line, a time profile of motion information is provided for one or more depths. Transmissions along different scan lines to monitor a same shear wave are avoided during formation of the temporal profile to provide higher temporal resolution, but interleaved or shifting scanning positions may be provided.

Other methods of detecting the pseudo shear wave with or without determining displacement of tissue may be used. The pseudo shear wave may be measured by determining tissue velocity and/or acceleration. Any elasticity or strain detection may be used. Correlation lag, maximum energy, maximum slope or other information may be calculated from ultrasound data to detect the pseudo shear wave.

The pseudo shear wave is detected to determine the timing of the wave passing the locations. Using displacement, the temporal profile for a given location indicates detection of the shear wave. The profile is examined for a non-noise or instance of variation. A peak or other location in the profile, with or without temporal low pass filtering, indicates the passing of the pseudo shear wave front.

In act 38, the shear velocity is calculated from the detected pseudo shear wave. A processor calculates the shear velocity from the apparent velocity of the pseudo shear wave traveling along the line. In act 40, the apparent velocity is calculated. In act 42, the apparent velocity is scaled, resulting in the shear wave velocity.

The apparent velocity of the pseudo wave and resulting shear velocity are determined in acts 40 and 38 in response to a single event of the transmitting. The location of the pseudo shear wave at different times is determined in response to just one transmission for generation of the shear wave. Other transmissions for monitoring are used to locate the pseudo shear wave. The transmission of act 32 to generate the shear wave occurs once, yet the shear velocity may be detected even with measurements only along a line. The transmission to generate the shear wave may not be repeated while still determining a shear velocity for the location. The calculations are performed in response to a single transmission to generate the shear wave. In alternative embodiments, the transmission of act 32 is repeated, such as repeating along the same line to determine velocity or to determine multiple velocities from multiple shear waves.

In act 40, the apparent velocity along the line is calculated. An apparent velocity of the pseudo shear wave traveling along the line is determined. In one embodiment, the apparent velocity is determined based on timing of the pseudo shear wave. The times at which the pseudo shear wave is detected at different locations and the length or distance between the locations are used to calculate the apparent velocity. For example, a velocity value is identified from the travel time of the peak to each spatial location. As another example, the apparent velocity is obtained by determining a time from generation of the shear wave until detection of the pseudo shear wave at a location spaced from the focal region. The time and distance to the location determine the apparent velocity. The distance is known from the scan line sampling (i.e., the position along the scan line or beam). The time is known from the relative time between generation and detection of the pseudo shear wave or between detection of the pseudo shear wave at different locations. The system clock or other time source indicates the relevant time.

Other techniques may be used to detect the peak in the profile in act 36 and/or estimate apparent velocity in act 40. For example, a regression is applied. Since the pseudo shear wave velocity is linear, a robust linear regression with automated outlier detection may indicate the apparent velocity in act 40. The ultrasound data for all of the sample points along the line is plotted for distance as a function of time or by time and distance. The linear regression is applied to the plot or data, providing a line fit to the data. The slope of the line indicates the apparent velocity.

Other approaches may be used. For example, data from different times is correlated to detect the shift in tissue caused by the pseudo shear wave. As another example, a feature is extracted from the temporal profiles. Principal component decomposition may be used. A correlation between the different temporal profiles is performed. The lag associated with the different distances for the different temporal profiles provides the apparent velocity. Alternatively, a wavelet analysis may be performed. A wavelet transform is applied to the temporal profiles to identify a peak corresponding to the pseudo shear wave.

In act 42, the velocity of the apparent wave is scaled to determine the shear wave velocity. Different transmit F numbers (F#) for the generation of the shear wave may result in different apparent velocities. By normalizing for F#, a weight may be applied to convert the apparent velocity of the pseudo shear wave to a shear wave velocity.

The F# is determined for the transmission of act 32. The F# is the depth to the focal region divided by the aperture width. The F# is determined from the beamforming parameters. The F# may be predetermined and stored or may be determined based on a current configuration or use.

Figure 4:
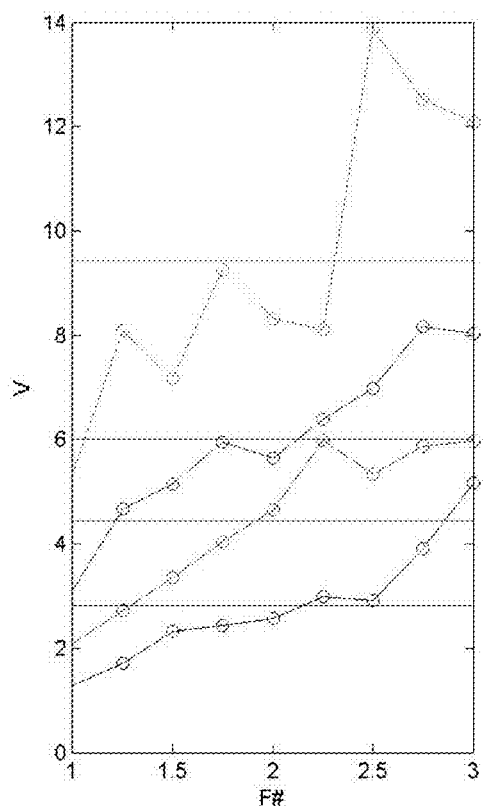
FIG. 4 is an example graph showing apparent velocity as a function of F#.
Figure 5:
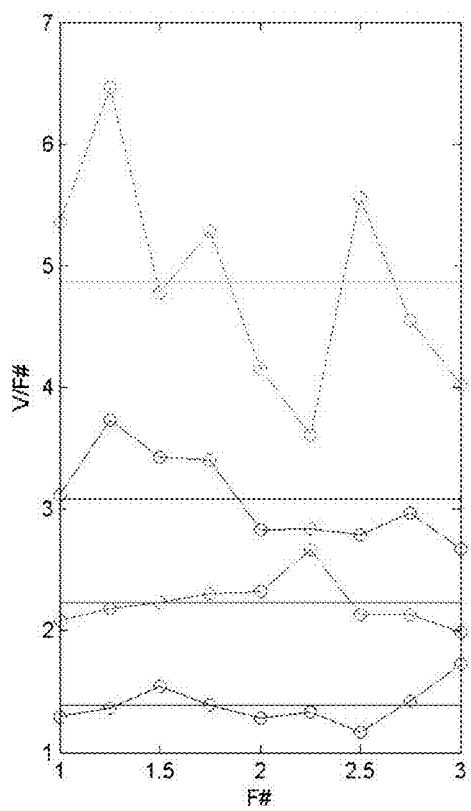
FIG. 5 is an example graph showing apparent velocity normalized by F#.

The constant to associate the normalized apparent velocity with a shear wave velocity is determined experimentally. FIG. 4 shows a graph of apparent velocity as a function of F#. The apparent velocities are obtained from phantoms with known shear wave velocities. FIG. 5 represents the normalization of the apparent velocities by the F#. The apparent velocity for each of the phantoms is steady for different F#s. Apparent velocity variations may increase as the apparent velocity increases due various factors, such as setting a window of detection for one or more locations offset from optimum or inaccurate time-to-peak detection. With positioning the sampling window for detecting the pseudo shear wave and averaging or using different processes to detect the shear wave, less variation may result. These examples result in a quantifiable constant relating normalized apparent velocity to the shear wave velocity. In the examples of FIGS. 4 and 5, the averaged F# adjusted shear velocities for each phantom (from lowest to highest) are 1.4, 2.2, 3.1, and 4.9 m/s. The actual calibrated shear velocities for the phantoms are 1.32, 1.82, 2.28, and 3.38 m/s. Thus, an average scale factor of 1.26 is used to calculate the actual shear wave velocity from the apparent velocity. Other scale factors may be provided.

In alternative embodiments, modeling is used to determine the scale factor. In vivo studies may alternatively be used. Other phantoms may be used. Combinations of different experiments and/or modeling may be used to determine the scale factor. An analytical function may be derived to determine the scale factor. This function may include the F/# and/or excitation aperture dimensions as input variables.

In act 42, the apparent velocity is scaled by the scale factor. The velocity of the pseudo shear wave is scaled by the constant and an inverse of the F#. By normalizing for F# and weighting by the constant, the shear wave velocity is determined from the apparent velocity. The calculation is represented as: Vshear=Vonaxis*K/(F#), where K is the constant (e.g., 1.26), Vshear is the shear wave velocity, and Vonaxis is the apparent velocity.

The shear wave velocity is calculated from a single excitation for generating the shear wave. The apparent velocity of the pseudo shear wave is determined on the axis of the transmission or other line rather than between laterally spaced scan lines. The shear velocity may be calculated using one shear wave generating transmission and monitoring along a single line. This reduces the need for multiple shear waves to calculate a shear modulus. The patient is subjected to less high amplitude acoustic radiation force transmissions.

A single shear velocity is calculated. Additional shear wave velocities may be determined along the same line or along different lines. Additional shear wave velocities may be determined in response to the same shear wave or in response to other shear waves. A plurality of shear velocities may be calculated for the region of interest. The results may be averaged or otherwise combined. For example, linear regression is applied to ten or other number of subsets. Each subset includes data for different depth ranges, such as each subset including data for twenty different depths. Shear velocity is determined for each subset. The average shear velocity is used. A variance or other statistical information may be derived from the different shear velocities. Alternatively, a spatial representation of shear wave velocity variance within the region of interest may be provided.

The shear velocity may be used for diagnosis or imaging. In other embodiment, a shear modulus or other characteristic of shear is calculated from the shear velocity.

In act 44, an image is displayed. The image is a function of the shear velocity. For example, the image includes text indicating the shear wave velocity or other shear characteristic calculated from the shear wave velocity. The shear wave velocity may be displayed on an anatomical representation or without the anatomical representation. A representation of shear velocity may be used instead of an actual number, such as mapping a color or otherwise modulating the pixels at the region of interest as a function of the shear velocity. For example, a high velocity is mapped to a brighter red than a lower velocity. Shear information, such as the shear velocity, may be indicated relative to a scan representation of the patient, such as an ultrasound image. The region of interest may be indicated with color or other coding of the shear velocity for the region indicated. A marker may be displayed for one or more locations. The shear velocity is provided as a bubble indication or text in reference to the marker.

The shear velocity may be indicated relative to a range of shear velocities with or without other shear velocity information. For example, a bar, line, graph or other representation of a range of shear velocities is displayed. The range may be for tissue or may be specific to type of tissue. For example, the user inputs or a processor identifies the type of tissue for which shear wave velocity is measured. A range of normal and abnormal velocities for that type of tissue is output. The range does or does not indicate normal or abnormal velocities. The estimated shear wave velocity is shown on the range, such as an arrow or other indicator of the estimated shear velocity range. The relative position may be more intuitive to a user.

The shear wave velocity or a modulus derived from the shear velocity may be displayed. The shear information is used for any application, such as for cardiac imaging. Given the rapid change in position and stress on the heart or other cardiac structure during the heart cycle, rapid determination of the shear velocity at different times may be useful. Using a single transmission to generate the shear wave and monitoring along one line for each given shear velocity, the shear velocity may be determined at multiple times during a single heart cycle. The transmission, generation, detection, and calculation of FIG. 1 may be repeated throughout the cycle to determine shear wave velocity at different times. Since only one scan line is needed, ultrasound systems not capable of multi-beam receive operation may be used.

Figure 6:
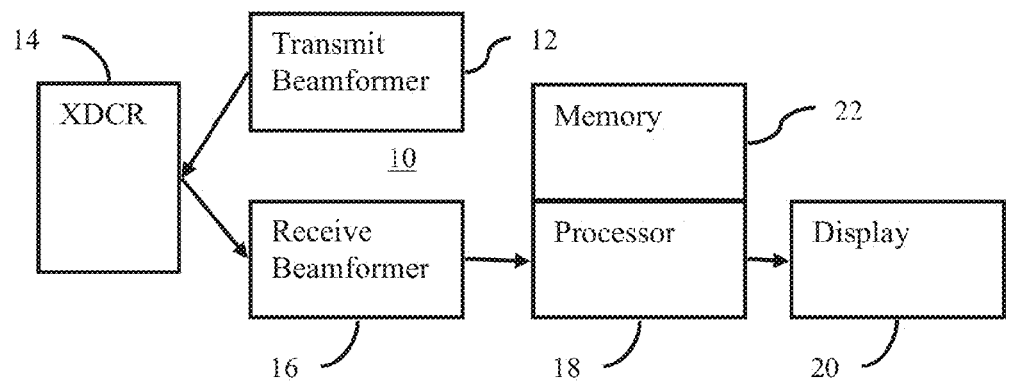
FIG. 6 is a block diagram of one embodiment of an ultrasound system for shear wave imaging.

FIG. 6 shows one embodiment of a system 10 for shear wave imaging in medical diagnostic ultrasound. The system 10 implements the method of FIG. 1 or other methods. The system 10 includes a transmit beamformer 12, a transducer 14, a receive beamformer 16, an image processor 18, a display 20, and a memory 22. Additional, different or fewer components may be provided. For example, a user input is provided for manual or assisted selection of display maps, tissue properties to be determined, region of interest selection, or other control. The system 10 is a medical diagnostic ultrasound imaging system. In alternative embodiments, the system 10 is a personal computer, workstation, PACS station, or other arrangement at a same location or distributed over a network for real-time or post acquisition imaging, so may not include the beamformers 12, 16 and transducer 14.

The transmit beamformer 12 is an ultrasound transmitter, memory, pulser, analog circuit, digital circuit, or combinations thereof. The transmit beamformer 12 is operable to generate waveforms for a plurality of channels with different or relative amplitudes, delays, and/or phasing. Upon transmission of acoustic waves from the transducer 14 in response to the generated waves, one or more beams are formed, such as a single beam for generating a shear wave. A sequence of transmit beams are generated to scan a one, two or three-dimensional region. Sector, Vector®, linear, or other scan formats may be used. The same region is scanned multiple times. For flow or Doppler imaging and for strain imaging, a sequence of scans is used. In Doppler imaging and shear velocity estimation, the sequence may include multiple beams along a same scan line with or without also transmitting along other scan lines. For strain imaging, scan or frame interleaving may be used (i.e., scan the entire region before scanning again). In alternative embodiments, the transmit beamformer 12 generates a plane wave or diverging wave for more rapid scanning.

The transmit beams are formed at different energy or amplitude levels. Amplifiers for each channel and/or aperture size control the amplitude of the transmitted beam. A transmit beam to generate a shear wave and/or for strain imaging may have a greater amplitude than for imaging or monitoring for the pseudo shear wave.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. Receive signals are generated in response to ultrasound energy (echoes) impinging on the elements of the transducer. The elements connect with channels of the transmit and receive beamformers 12, 16.

The receive beamformer 16 includes a plurality of channels with amplifiers, delays, and/or phase rotators, and one or more summers. Each channel connects with one or more transducer elements. The receive beamformer 16 applies relative delays, phases, and/or apodization to form one or more receive beams in response to a transmission. Dynamic focusing may be provided. The delayed and apodized signals from the different channels are summed. In alternative embodiments, the receive beamformer 16 is a processor for generating samples using Fourier or other transforms.

The receive beamformer 16 may include a filter, such as a filter for isolating information at a second harmonic or other frequency band relative to the transmit frequency band (e.g., the fundamental frequency). Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental or other band.

The receive beamformer 16 outputs beam summed data representing spatial locations. Data for a single location, locations along a line, locations for an area, or locations for a volume are output. The data may be for different purposes. For example, different scans are performed for B-mode or tissue data than for shear wave velocity estimation. Data received for B-mode or other imaging may be used for estimation of shear velocity. For shear velocity estimation in one embodiment, the receive beamformer 16 is configured to receive along a single line, such as a common transmit and receive scan line extending from the center of an aperture to a transmit focal region. The receive beamformer 16 receives signals and outputs data for monitoring along the scan line after and in response to the transmit event to generate the shear wave.

The processor 18 is a B-mode detector, Doppler detector, pulsed wave Doppler detector, correlation processor, Fourier transform processor, application specific integrated circuit, general processor, control processor, image processor, graphics processing unit, field programmable gate array, digital signal processor, analog circuit, digital circuit, network, server, group of processors, data path, combinations thereof or other now known or later developed device for detecting and processing information for calculating shear velocity from beamformed ultrasound samples. In one embodiment, the processor 18 includes one or more detectors and a separate processor. The processor 18 is operable to estimate shear wave velocity. For example, the processor 18 performs any combination of one or more of the acts shown in FIG. 1.

The processor 18 estimates shear velocity by detecting a time for a pseudo shear wave to travel a distance along a line or towards the transducer. The apparent velocity of the pseudo shear wave is estimated from data representing return from along the line. Multiple estimates may be provided and/or data from different locations used for one estimate.

The propagation velocity of the pseudo shear wave is estimated by the processor 18. Linear regression, correlation, principle component extraction, wavelet transforms, displacement detection, or other estimation techniques may be used to estimate the apparent velocity of a pseudo shear wave. Any or no validation of the estimate may be performed by the processor 18.

The processor 18 converts the apparent velocity to a shear wave velocity. Any conversion function may be used. With a look-up table or using a mathematical relationship, the apparent velocity of the pseudo shear wave is converted to the shear wave velocity. In one embodiment, the shear wave velocity is estimated by weighting the propagation velocity by a transmission F number. For example, the apparent velocity is normalized by F# and multiplied by a constant. Other functions may be used. A result of the weighting is the shear wave velocity. The shear wave velocity is calculated without lateral sampling or tracking of the lateral movement of the shear wave.

In one embodiment, the processor 18 implements a classifier. Through programming or machine learning, the classifier distinguishes between diseased and non-diseased tissue. The classifier is specific to a type of tissue, accounts for the type of tissue, or is generic to the type of tissue. The classifier scores the disease level based, at least in part, on the shear wave velocity. Any score system may be used, such as a single threshold. If the velocity is above or below the threshold for a given type of tissue, then the tissue is diseased. More complex scoring may be used, such as associated with clinical studies distinguishing between stages or types of disease based, at least in part, on the shear velocity. The score (e.g., level 1-5) may be output.

The processor 18 generates display data, such as graphic overlays and images. The display data is in any format, such as values before mapping, gray scale or color-mapped values, red-green-blue (RGB) values, scan format data, display or Cartesian coordinate format data, or other data. The processor 18 outputs data appropriate for the display device 20.

The display data is for an image. The image may include a scan image or information representing the patient, such as an ultrasound image. The image may include text. The image is generated as a function of the shear velocity. The shear velocity may be displayed in the image as text adjacent to or over the ultrasound image. The shear velocity may be displayed as a bar, graph, or text value with other text information or alone. The shear velocity may be displayed as a color, overlay, or other modulation of the ultrasound image.

The processor 18 operates pursuant to instructions stored in the memory 22 or another memory. The processor 18 is programmed for shear wave imaging in medical diagnostic ultrasound. The memory 22 is a computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display device 20 is a CRT, LCD, projector, plasma, printer, or other display for displaying an image with shear velocity information, graphics, user interface, two-dimensional images, or three-dimensional representations. The display device 20 displays ultrasound images, the shear velocity, and/or other information. The displayed information is in a report or screen presentation.

In one embodiment, the display device 20 outputs an image of a region of the patient, such as a two-dimensional elasticity, Doppler tissue, or B-mode image. The image may include a location indicator for the shear velocity. The location relative to the imaged tissue for which shear velocity is calculated is shown. The shear velocity or modulus is provided on or adjacent the image of the region. Other images may be displayed.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for shear wave imaging in medical diagnostic ultrasound, the method comprising:
   transmitting, from a transducer, acoustic energy to a focal region;
   generating a shear wave from the transmitting;
   detecting a pseudo shear wave at a plurality of locations along a line extending from the transducer, the pseudo shear wave formed with the shear wave;
   calculating, with a processor, a shear velocity from the detected pseudo shear wave in response to a single event of the transmitting and without repeating the transmitting; and
   displaying an image as a function of the shear velocity.

2. The method of claim 1 wherein transmitting comprises transmitting acoustic radiation force.

3. The method of claim 1 wherein generating comprises generating the shear wave as a laterally propagating wave, and wherein detecting the pseudo shear wave comprises detecting an apparent wave propagating towards the transducer.

4. The method of claim 1 wherein detecting comprises determining a timing of displacement occurring at the plurality of locations due to the pseudo shear.

5. The method of claim 1 wherein calculating comprises:
determining an F number for the transmitting;
calculating a pseudo shear wave velocity along the line; and
scaling the pseudo shear wave velocity by a constant and an inverse of the F number, a result of the scaling comprising the shear velocity.

6. The method of claim 1 wherein transmitting comprises transmitting once along the line, detecting comprises detecting in response to the one transmitting, and wherein calculating comprises calculating from data responsive to the one transmitting and representing only the line.

7. The method of claim 1 wherein displaying comprises generating the image with text representing the shear velocity.

8. The method of claim 1 wherein displaying comprises generating a one or two-dimensional representation of shear information, the shear information being a function of the shear velocity.

9. The method of claim 1 wherein displaying comprises:
displaying a representation of a two-dimensional region of a patient with a location marker at the focal region; and
displaying the shear velocity as associated with the location marker on the image.

10. The method of claim 1 further comprising repeating the transmitting, generating, detecting, and calculating for cardiac imaging.

11. In a non-transitory computer readable storage medium having stored therein data representing instructions executable by a programmed processor for shear wave characterization in medical diagnostic ultrasound, the storage medium comprising instructions for:
tracking a pseudo shear wave along a line substantially parallel with a scan line;
determining an apparent velocity of the pseudo shear wave along the line; and
scaling the apparent velocity by a constant and a transmit F number, a result of the scaling comprising a shear velocity, and wherein the instructions further comprise displaying an image as a function of the shear velocity.

12. The non-transitory computer readable storage medium of claim 11 wherein tracking comprises determining temporal profiles for each of a plurality of locations on the line, and wherein determining the apparent velocity comprises determining a timing for the locations from the temporal profiles.

13. The non-transitory computer readable storage medium of claim 11 wherein tracking and determining comprise tracking and determining in response to a single transmission.

14. The non-transitory computer readable storage medium of claim 11 wherein tracking comprises tracking along the scan line of the wave as the wave appears to propagate towards a transducer.

15. The non-transitory computer readable storage medium of claim 11 wherein tracking comprises tracking the wave as an associated shear wave travels substantially perpendicularly to the scan line.

16. The non-transitory computer readable storage medium of claim 11 wherein scaling comprises dividing the apparent velocity by the transmit F number.

17. A method for shear wave imaging in medical diagnostic ultrasound, the method comprising:
locating an apparent wave traveling towards a transducer in a patient, the apparent wave being responsive to a shear wave traveling laterally relative to the transducer;
calculating, with a processor, a shear velocity from the apparent wave; and
displaying an image as a function of the shear velocity.

18. The method of claim 17 wherein locating and calculating are performed in response to a single transmission along a scan line, the locating being along the scan line.

19. The method of claim 17 wherein calculating comprises:
calculating an apparent velocity of the apparent wave; and
multiplying the apparent velocity by a constant and an inverse of a transmit F number.

20. A system for shear wave velocimetry in medical diagnostic ultrasound, the system comprising:
a beamformer configured to receive along a single scan line in response to a single transmit event and transmit acoustic energy in a transmit event;
a processor configured to estimate a shear velocity from data representing response along the scan line and by determining a propagation velocity of an apparent wave traveling towards a transducer and weighting the propagation velocity by a transmission F number of the transmit event, a result of the weighting comprising the shear velocity; and
a display device configured to output an image as a function of the shear velocity.

* * * * *